United States Patent
Oguro et al.

(10) Patent No.: US 11,040,941 B2
(45) Date of Patent: Jun. 22, 2021

(54) ALKANETHIOIC ACID DERIVATIVE AND PERFUME COMPOSITION CONTAINING THE SAME

(71) Applicant: T. HASEGAWA CO., LTD., Tokyo (JP)

(72) Inventors: Daichi Oguro, Kanagawa (JP); Kazuya Kawabata, Kanagawa (JP); Akira Nakanishi, Kanagawa (JP); Toshifumi Nozawa, Kanagawa (JP); Masaki Shimazu, Kanagawa (JP)

(73) Assignee: T. HASEGAWA CO., LTD., Tokyo (JP)

( * ) Notice: Subject to any disclaimer, the term of this patent is extended or adjusted under 35 U.S.C. 154(b) by 0 days.

(21) Appl. No.: 16/760,557

(22) PCT Filed: Sep. 12, 2018

(86) PCT No.: PCT/JP2018/033739
§ 371 (c)(1),
(2) Date: Apr. 30, 2020

(87) PCT Pub. No.: WO2019/087580
PCT Pub. Date: May 9, 2019

(65) Prior Publication Data
US 2020/0290958 A1     Sep. 17, 2020

(30) Foreign Application Priority Data

Nov. 6, 2017 (JP) .............................. JP2017-213898

(51) Int. Cl.
*C07C 327/22* (2006.01)
*A23L 27/20* (2016.01)
*A61K 8/46* (2006.01)
*C11B 9/00* (2006.01)

(52) U.S. Cl.
CPC ........ *C07C 327/22* (2013.01); *A23L 27/2022* (2016.08); *A61K 8/46* (2013.01); *C11B 9/0011* (2013.01)

(58) Field of Classification Search
CPC ..... C07C 327/22; A23L 27/2022; A61K 8/46; C11B 9/0011
See application file for complete search history.

(56) References Cited

U.S. PATENT DOCUMENTS

| 4,296,137 A | 10/1981 | Boden |
| 2011/0282089 A1 | 11/2011 | Inaba et al. |

FOREIGN PATENT DOCUMENTS

| JP | 2001-112431 | 4/2001 |
| JP | 2010-100570 | 5/2010 |
| JP | 2011-83264 | 4/2011 |
| JP | 2011-236185 | 11/2011 |
| JP | 4931900 | 5/2012 |
| JP | 4931901 | 5/2012 |
| JP | 6076037 | 2/2017 |
| WO | 2016/102424 | 6/2016 |
| WO | 2016/102425 | 6/2016 |

OTHER PUBLICATIONS

STN Registry database entry for CAS RN 2180135-09-3, Entered STN Feb. 26, 2018, Accessed Oct. 1, 2020.*
STN Registry database entry for CAS RN 2180135-08-2, Entered STN Feb. 26, 2018, Accessed Oct. 1, 2020.*
International Search Report dated Dec. 19, 2018 in International (PCT) Application No. PCT/JP2018/033739.

* cited by examiner

*Primary Examiner* — Alicia L Otton
(74) *Attorney, Agent, or Firm* — Wenderoth, Lind & Ponack, L.L.P.

(57) ABSTRACT

An alkanethioic acid derivative capable of imparting a characteristic aroma or flavor to fragrances and cosmetics, and foods and beverages; and a perfume composition comprising the alkanethioic acid derivative as an active ingredient. S-alkyl 5-[(1-alkoxy)ethoxy]alkanethioate represented by formula (1), and a perfume composition comprising the S-alkyl 5-[(1-alkoxy)ethoxy]alkanethioate represented by formula (1) as an active ingredient. In the formula (1), $R_1$ represents an alkyl group having 1 to 9 carbon atoms, $R_2$ represents an alkyl group having 2 to 4 carbon atoms, and $R_3$ represents a methyl group or an ethyl group.

5 Claims, No Drawings

ALKANETHIOIC ACID DERIVATIVE AND PERFUME COMPOSITION CONTAINING THE SAME

TECHNICAL FIELD

The present invention relates to a novel alkanethioic acid derivative which is useful as a perfume compound or the like and a perfume composition comprising the said derivative as an active ingredient.

BACKGROUND ART

In recent years, consumers' tastes have diversified, and accordingly, foods and beverages having various kinds of aromas have been manufactured. For example, in the food and beverage industry, various technological developments have been demanded to meet the needs for foods and drinks having tastiness which suits the tastes of consumers, an aroma and flavor with a natural feeling.

With regard to flavors, which are one raw material for foods and beverages, the needs have not been sufficiently met by only the conventionally proposed perfume compounds. Therefore, the development of a perfume composition having unique flavor characteristics that have not been found in the past and having not only flavor characteristics but also excellent sustainability thereof has been a problem to be solved.

Also, with regard to fragrances and cosmetics, with the diversification of consumer preferences, development of various types of fragrances and cosmetics is desired. In the perfume used in fragrances and cosmetics, there is an ever-increasing demand for materials with a novel aroma, and the current situation is that the combination of conventional perfume substances does not sufficiently meet the demand. Therefore, demands for new perfume materials are increasing.

So far, several proposals for improving aroma have been made. For example, Patent Document 1 discloses that by including an optically active or racemic cis-6-dodecene-4-olide, a long-lasting sweet fermentation feeling of fermented foods and beverages is enhanced. However, the effect is limited to fermented foods and beverages.

Also, by adding 2-methyl-3-thiophenethiol or 3-mercapto-3-methylbutylformate to foods and beverages, the sesame-like freshly roasted feeling, freshly ground feeling, and oily feeling are enhanced. (Patent Documents 2 and 3). However, although these compounds enabled increasing sesame-like specific aromas, it was difficultly said that using the compounds widely for increasing general aromas led to good results as compared with the effect of imparting sesame-like aromas.

Also, δ-lactones are known as perfume compounds, and Patent Document 4 discloses that δ-lactones enhance the feeling of fats and oils. However, since δ-lactones are known perfume compounds, it has been difficult to impart a unique aroma that was not found in conventional perfume compounds.

Further, Patent Document 5 discloses that specific dithioethers (e.g., furfurylmethyl disulfide, methyl 2-methyl-3-furyl disulfide and difurfuryl disulfide) are added to soy sauce or a soy sauce flavor imparting agent so that the fermentation and ripening feeling of soy sauce are obtained. However, since it is effective only for specific foods and beverages, satisfactory results have not been obtained even when used for general foods and beverages or fragrances and cosmetics.

Therefore, it is necessary to present a perfume compound which gives a better effect on imparting an aroma such as a fat and oil sensation, a fat sensation, a fermentation sensation, a rich sensation and a fresh sensation to fragrances and cosmetics or foods and beverages.

PRIOR ART

Patent Documents

Patent Document 1: Japanese Patent Laid-Open No. 2001-112431
Patent Document 2: Japanese Patent No. 4931900
Patent Document 3: Japanese Patent No. 4931901
Patent Document 4: Japanese Patent Laid-Open No. 2011-83264
Patent Document 5: Japanese Patent No. 6076037

SUMMARY OF THE INVENTION

Problems to be Solved by the Invention

An object of the present invention is to provide a novel alkanethioic acid derivative that can impart aroma and flavor to fragrances and cosmetics or foods and beverages, and a perfume composition comprising the said derivative as an active ingredient.

Means for Solving the Problem

The present inventors have conducted intensive studies to solve the above-mentioned problems, and as a result, obtained by converting alkyl 5-[(1-alkoxy)ethoxy] alkanoate to thioacid, S-alkyl 5-[(1-alkoxy)ethoxy alkanethioate (1) has an oily feeling, a fatty feeling, a fermenting feeling, a rich feeling, a fresh feeling, onion-like, meat-like, or other aroma characteristics. Furthermore, it has been found that by adding the compound itself or a perfume composition containing the compound to fragrances and cosmetics or foods and beverages, it is possible to improve or enhance the aroma and flavor. Thus, the present invention has been completed.

Accordingly, the following subject matters are disclosed herein. Such subject matters are also called disclosures.

Subject 1: An S-alkyl 5-[(1-alkoxy)ethoxy]alkanethioate represented by the following formula (1):

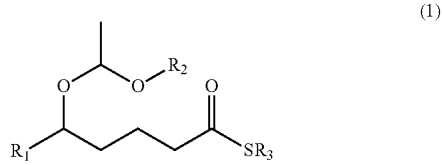

(1)

wherein $R_1$ represents an alkyl group having 1 to 9 carbon atoms, $R_2$ represents an alkyl group having 2 to 4 carbon atoms, and $R_3$ represents a methyl group or an ethyl group.

Subject 2: A perfume composition comprising, as an active ingredient, an S-alkyl 5-[(1-alkoxy)ethoxy]alkanethioate represented by the following formula (1):

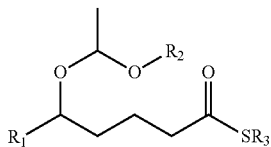

(1)

wherein $R_1$ represents an alkyl group having 1 to 9 carbon atoms, $R_2$ represents an alkyl group having 2 to 4 carbon atoms, and $R_3$ represents a methyl group or an ethyl group.

Subject 3: A composition comprising:

an S-alkyl 5-[(1-alkoxy)ethoxy]alkanethioate represented by the following formula (1):

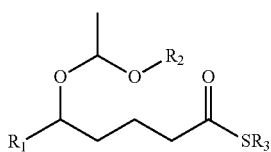

(1)

wherein $R_1$ represents an alkyl group having 1 to 9 carbon atoms, $R_2$ represents an alkyl group having 2 to 4 carbon atoms, and $R_3$ represents a methyl group or an ethyl group; and a diluent.

Subject 4: A fragrance and cosmetic or a food and beverage, comprising the compound of subject 1.

Subject 5: A fragrance and cosmetic or a food and beverage, comprising the composition of subject 2 or 3.

Subject 6: An S-alkyl 5-[(1-alkoxy)ethoxy]alkanethioate represented by the following formula (1):

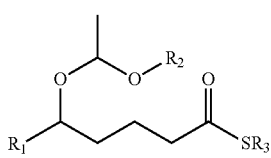

(1)

wherein $R_1$ represents an alkyl group having 1 to 9 carbon atoms, $R_2$ represents an alkyl group having 2 to 4 carbon atoms, and $R_3$ represents a methyl group or an ethyl group, for use in imparting an aroma or a flavor to a fragrance and cosmetic or a food and beverage.

Subject 7: A method for imparting an aroma or a flavor to a fragrance and cosmetic or a food and beverage, or increasing an aroma or a flavor, comprising:

a step of adding, to the fragrance and cosmetic or the food and beverage in need of impartment or increasing of the aroma or the flavor, an effective amount of an S-alkyl 5-[(1-alkoxy)ethoxy]alkanethioate represented by the following formula (1):

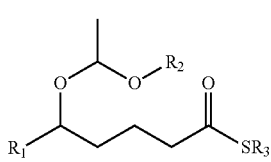

(1)

wherein $R_1$ represents an alkyl group having 1 to 9 carbon atoms, $R_2$ represents an alkyl group having 2 to 4 carbon atoms, and $R_3$ represents a methyl group or an ethyl group.

Effects of the Invention

The S-alkyl 5-[(1-alkoxy)ethoxy] alkanethioates of the present invention have a characteristic aroma and, when mixed with other perfume compounds, add unique aroma characteristics to the perfume composition, thus its aroma and flavor can be improved or enhanced. In addition, by adding the perfume composition containing an S-alkyl 5-[(1-alkoxy)ethoxy] alkanethioate to a food and drink, a unique aroma characteristic is added to the target product. Therefore, it is possible to provide a variety of fragrances and cosmetics or foods and drinks that have a characteristic of improving or enhancing the aroma and flavor, and are rich in a variety of tastes suitable for consumers.

EMBODIMENTS FOR CARRYING OUT THE INVENTION

Contents or subjects disclosed herein will be described in detail hereinafter.

Examples of the compound represented by the formula (1) or an S-alkyl 5-[(1-alkoxy)ethoxy]alkanethioate include S-methyl 5-[(1-ethoxy)ethoxy]hexanethioate, S-methyl 5-[(1-ethoxy)ethoxy]octanethioate, S-methyl 5-[(1-ethoxy)ethoxy]decanethioate, S-methyl 5-[(1-ethoxy)ethoxy]octanethioate, S-methyl 5-[(1-ethoxy)ethoxy]dodecanethioate, S-methyl 5-[(1-ethoxy)ethoxy]tetradecanethioate, S-methyl 5-[(1-propoxy)ethoxy]tetradecanethioate, S-methyl 5-[(1-butoxy)ethoxy]decanethioate, S-methyl 5-[(1-butoxy)ethoxy]tetradecanethioate, S-ethyl 5-[(1-ethoxy)ethoxy]decanethioate, S-ethyl 5-[(1-ethoxy)ethoxy]tetradecanethioate and S-ethyl 5-[(1-butoxy)ethoxy]decanethioate.

Examples of a typical compound include S-methyl 5-[(1-ethoxy)ethoxy]alkanethioate represented by the following formula (2):

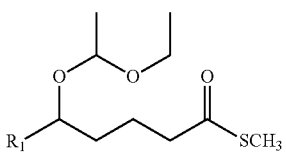

(2)

wherein $R_1$ represents an alkyl group having 1 to 9 carbon atoms.

Examples of a further typical compound include S-methyl 5-[(1-ethoxy)ethoxy]decanethioate and S-methyl 5-[(1-ethoxy)ethoxy]tetradecanethioate. Although it is preferable to use such typical compounds as perfume compounds, it is not limited to these.

The S-alkyl 5-[(1-alkoxy)ethoxy]alkanethioate represented by the formula (1) can be produced, for example, according to reaction routes shown in the following reaction scheme 1 and reaction scheme 2.

Reaction Scheme 1

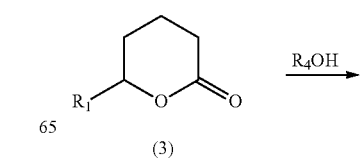

(3)

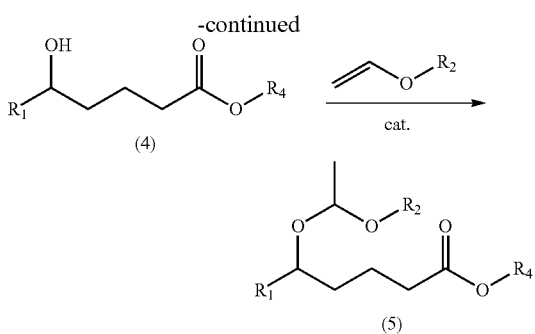

in the formulas (3) to (5), $R_1$ represents an alkyl group having 1 to 9 carbon atoms, $R_2$ represents an alkyl group having 2 to 4 carbon atoms, and $R_4$ represents a methyl group or an ethyl group.

In the first step of the above reaction, a transesterification reaction is applied to the δ-lactone to carry out a ring opening reaction of an intramolecular ester bond to obtain a hydroxyester. For example, a method of reacting with methanol or ethanol can be exemplified.

In the second step of the above reaction, an acetalization reaction can be applied to the hydroxyl group of the hydroxyester obtained in the first step. For example, a method of performing an exchange reaction with acetaldehyde dialkyl acetal in the presence of an acid catalyst, and a method of more simply reacting with an alkyl vinyl ether in the presence of an acid catalyst can be exemplified.

Reaction Scheme 2

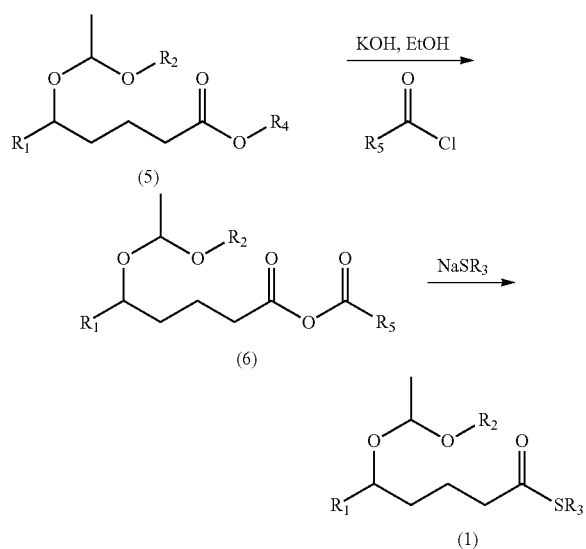

in the formulas (5) to (6), $R_1$ represents an alkyl group having 1 to 9 carbon atoms, $R_2$ represents an alkyl group having 2 to 4 carbon atoms, $R_3$ represents a methyl group or an ethyl group, $R_4$ represents a methyl group or an ethyl group, and $R_5$ represents an alkyl group having 1 to 6 carbon atoms.

In the third step of the above-mentioned reactions, a carboxylate obtained by saponifying the alkyl 5-[(1-alkoxy) ethoxy]alkanoate obtained in the second step in the presence or the absence of an alkali and an alcohol is reacted with an acyl halide to obtain a 5-[(1-alkoxy)ethoxy]alkanoic acid anhydride. For example, a potassium carboxylate obtained in the presence of potassium hydroxide and ethanol is reacted with the acyl chloride to obtain the 5-[(1-alkoxy) ethoxy]alkanoic acid anhydride.

Moreover, in the fourth step of the above-mentioned reactions, an S-alkyl 5-[(1-alkoxy)ethoxy]alkanethioate which is one of the disclosures herein can be obtained by a reaction with sodium alkanethiolate.

Although details of each step will be described hereinafter, the subjects or the disclosures herein are not intended to be limited to these contents.

The δ-lactone of the formula (3) used as the starting material of the first step may be either δ-lactones synthesized according to a common method or commercially available products. Examples of the commercially available product include δ-hexalactone (produced by Tokyo Chemical Industry Co., Ltd.), δ-octalactone (produced by Tokyo Chemical Industry Co., Ltd.), δ-nonalactone (produced by Sigma-Aldrich Co. LLC.), δ-decalactone (produced by Tokyo Chemical Industry Co., Ltd.), δ-undecalactone (produced by Sigma-Aldrich Co. LLC.), δ-dodecalactone (produced by Sigma-Aldrich Co. LLC.), δ-tridecalactone (produced by Tokyo Chemical Industry Co., Ltd.) and δ-tetradecalactone (produced by Tokyo Chemical Industry Co., Ltd.).

The δ-lactone is reacted with a sodium alkoxide in an alcohol solvent, the alkyl 5-hydroxyalkanoate represented by the formula (4) can be produced.

Methanol or ethanol can be used for the alcohol to be used, and the amount used is in the range of usually 1.0 to 200.0 mol, preferably 30.0 to 80.0 mol per 1 mol of the δ-lactone.

This reaction is performed at a temperature in the range of usually 70° C. to 90° C., preferably 75° C. to 85° C. for usually 30 minutes to 24 hours, preferably around 30 minutes to 12 hours.

Common post-treatment methods such as the neutralization of a basic substance and extraction from a reaction solvent are applied to a crude product containing the obtained compound (4), and the obtained alkyl 5-hydroxyalkanoate represented by the formula (4) is directly used for the following step.

In the following second step, the alkyl 5-hydroxyalkanoate represented by the formula (4) is reacted with an alkyl vinyl ether in an aprotic solvent using an acid catalyst, and an alkyl 5-[(1-alkoxy)ethoxy]alkanoate represented by the formula (5) can be produced.

The alkyl vinyl ether used in the second step may be either of alkyl vinyl ethers synthesized according to a common method and commercially available products. Examples of the commercially available product include ethyl vinyl ether (produced by Tokyo Chemical Industry Co., Ltd.), propyl vinyl ether (produced by Sigma-Aldrich Co. LLC.) and butyl vinyl ether (produced by Tokyo Chemical Industry Co., Ltd.).

The alkyl vinyl ether can be used in the range of usually 1.0 to 5.0 mol, preferably 1.5 to 3.5 mol per 1 mol of the alkyl 5-hydroxyalkanoate. The reaction method is preferably a method for dropwise addition of the alkyl vinyl ether, and the alkyl vinyl ether is added dropwise to the ethyl 5-hydroxyalkanoate at a temperature in the range of 0° C. to 20° C., preferably 0° C. to 15° C., over usually 5 minutes to 45 minutes, preferably around 10 minutes to 30 minutes. Although the reaction time is not particularly limited, a reaction for 1 hour or more is necessary after the dropwise addition of the alkyl vinyl ether.

As long as the solvent to be used is an aprotic solvent, the solvent is not particularly limited. A hydrocarbon solvent such as hexane or toluene; or an ether solvent such as diethyl ether or tetrahydrofuran can be used. The reaction proceeds by adding an acid catalyst. Examples of the acid catalyst to be used include benzenesulfonic acid, para-toluenesulfonic acid, pyridine salts thereof, and mineral acids such as concentrated sulfuric acid and phosphoric acid. Preferable examples include pyridine para-toluenesulfonate.

A crude product containing the obtained compound represented by the formula (5) is washed with an alkaline aqueous solution, the reaction solvent is collected, and alkyl 5-[(1-alkoxy)ethoxy]alkanoate can be isolated. The obtained formula (5) compound can be purified using means such as column chromatography and distillation under vacuum if needed.

In the following third step, a carboxylate obtained by adding potassium hydroxide and ethanol to the compound represented by the formula (5) and then saponifying the mixture is reacted with an acyl halide to obtain a 5-[(1-alkoxy)ethoxy]alkanoic acid anhydride represented by the formula (6). Examples of the acyl halide include benzoyl chloride, 2,4,6-trichlorobenzoyl chloride and pivaloyl chloride. Benzoyl chloride or pivaloyl chloride can be illustrated preferably.

The acyl halide to be used in the third step may be either of acyl halides synthesized by a common method and commercially available products. Examples of the commercially available product include benzoyl chloride (produced by Tokyo Chemical Industry Co., Ltd.) and pivaloyl chloride (produced by Wako Pure Chemical Corporation).

The acyl halide can be used in the range of usually 0.5 to 3.0 mol, preferably 0.5 to 2.0 mol per 1 mol of the alkyl 5-[(1-alkoxy)ethoxy]alkanoate. The reaction method is preferably a method for dropwise addition of the acyl halide to the carboxylate, and the dropwise addition is performed at a temperature in the range of 0° C. to 20° C., preferably 0° C. to 15° C., over usually 5 minutes to 45 minutes, preferably around 10 minutes to 35 minutes.

In the following fourth step, a sodium alkane thiolate is reacted with the compound represented by the formula (6), and an S-alkyl 5-[(1-alkoxy)ethoxy]alkanethioate represented by the formula (1) can be obtained. Examples of the sodium alkanethiolate include sodium methanethiolate and sodium ethanethiolate.

The sodium alkanethiolate to be used in the fourth step may be either of sodium alkanethiolates synthesized by a common method and commercially available products. Examples of the commercially available product sodium alkanethiolate include sodium methanethiolate (produced by Tokyo Chemical Industry Co., Ltd.) and sodium ethanethiolate (produced by Sigma-Aldrich Co. LLC.).

In the fourth step, a method of dropwise addition of the reaction liquid obtained in the third step into the sodium alkanethiolate charged beforehand is desirable, and the dropwise addition is performed at a temperature in the range of 5° C. to 25° C., preferably 10° C. to 20° C., over usually 5 minutes to 45 minutes, preferably around 10 minutes to 35 minutes. Although the reaction time is not particularly limited, the reaction for 1 hour or more is necessary after the reaction liquid is added dropwise. The end point of the reaction is preferably determined by GLC analysis.

The compound represented by the formula (1) and obtained in the reaction can be purified by a usual purification method, for example an operation such as distillation or silica gel chromatography.

In this specification, the term "aroma" (or aromas) is used to include a refreshing sensation, a burning sensation, a crisp feeling, and the like in addition to the scent received from the nasal cavity. On the other hand, "flavor" (or flavors) is a term similar to "aroma", but generally, when eating food, the nose, mouth, tongue, and throat receive the scent, taste. It is used separately from aroma because it includes various physical, chemical and sensory factors such as tactile sensation. In this specification, "fragrances and cosmetics" is an abbreviation for a scented product and a cosmetic, and is used to mean perfume other than a flavor.

The S-alkyl 5-[(1-alkoxy)ethoxy] alkanethioate represented by the formula (1) is characterized by having an oily feeling, a fatty feeling, a fermenting feeling, a rich feeling, a fresh feeling, an onion-like, and a meat-like aroma. Utilizing such characteristics, it can be added to fragrances and cosmetics or foods and beverages as it is to impart or enhance a characteristic aroma or flavor. The said alkanoate is, if necessary, as a composition comprising a diluent such as water, ethanol, propylene glycol, and vegetable oil, mixed with other components such as, citrus, fruit, mint, spice, nut, meat, milk-based, marine-based, vegetable-based, tea/coffee-based, vanilla-based, or the like to prepare a perfume composition for fragrances and cosmetics having citrus note, fruity note, woody note, or the like. Using the perfume composition, an aroma and flavor can also be imparted or increased to fragrances and cosmetics or foods and beverage.

Furthermore, two or more S-alkyl 5-[(1-alkoxy)ethoxy] alkanethioates represented by the formula (1) can also be mixed at any ratio and used, and the S-alkyl 5-[(1-alkoxy) ethoxy]alkanethioate can be also mixed with other perfume components and used. Examples of the other perfume components which can be contained with the S-alkyl 5-[(1-alkoxy)ethoxy]alkanethioate include synthetic perfumes, natural essential oils, natural perfumes, and animal and plant extracts described in "Japan Patent Office, Shuchi Kanyo Gijutsushu (Koryo) (Collection of Well-known Common Techniques (Perfume) in Japanese), Part II Food Perfume), pp. 7-87 published on Jan. 14, 2000" and "Japan Patent Office, Shuchi Kanyo Gijutsushu (Koryo) (Collection of Well-known Common Techniques (Perfume) in Japanese), Part III Scented Product and Cosmetic Perfume), pp. 49-103 published on Jun. 15, 2001".

Examples include: known perfume compounds such as hydrocarbons such as myrcene, camphene, limonene, terpinolene, cedrene, caryophyllene, longifolene and 1,3,5-undecatriene; alcohols such as ethanol, propanol, butanol, pentanol, isoprenol, hexanol, (Z)-3-hexen-1-ol, heptanol, octanol, 1-octen-3-ol, nonanol, 2,6-nonadienol, decanol, dodecanol, linalool, geraniol, nerol, citronellol, dihydromyrcenol, menthol, terpineol, farnesol, nerolidol, santalol, cedrol, benzyl alcohol, cinnamyl alcohol, phenylethyl alcohol, furfuryl alcohol, acetyl methyl carbinol and dimethyl benzyl carbinol aldehydes such as acetaldehyde, propanal, butanal, 2-butenal, hexanal, (E)-2-hexenal, octanal, 4-heptenal, 2,4-octadienal, nonanal, 2-nonenal, 2,4-nonadienal, 2,6-nonadienal, decanal, 2,4-decadienal, undecanal, 10-undecenal, 2,4-undecadienal, dodecanal, citronellal, citral, hydroxycitronellal, benzaldehyde, cinnamyl aldehyde, α-amylcinnamyl aldehyde, phenyl acetaldehyde, vanillin, ethyl vanillin, furfural and heliotropin; ketones such as 2-heptanone, 2-octanone, 3-octanone, 1-octen-3-one, 2-nonanone, 3-nonanone, 8-nonen-2-one, 2-undecanone, 2-tridecanone, acetoin, 5-hydroxy-4-octanone, diacetyl, 2,3-pentadione, 2,3-hexadione, 2,3-heptadione, carvone, menthone, nootkatone, dihydrojasmone, α-ionone, β-ionone, methyl ionone, α-damascone, β-damascenone, acetyl cedrene, raspberry ketone, p-methoxyacetophenone, benzophenone, maltol, ethyl maltol, cyclotene and 2,5-dimethyl- 4-hydroxy-3(2H)-furanone; esters such as ethyl formate, ethyl acetate, butyl acetate, isoamyl acetate, decyl acetate, dodecyl acetate, linalyl acetate, geranyl acetate, menthyl acetate, methyl dihydrojasmonate, phenethyl acetate, ethyl lactate, ethyl butyrate, ethyl 2-methylbutyrate, ethyl 3-ethylbutyrate, methyl valerate, methyl caproate, ethyl caproate, methyl heptanoate, ethyl heptanoate, ethyl caprylate, isoamyl caprylate, heptyl caprylate, methyl nonanoate, ethyl nonanoate, methyl caprate, ethyl caprate, ethyl undecanoate, methyl laurate, ethyl laurate, ethyl myristate, ethyl palmitate, methyl salicylate, diethyl succinate, diethyl sebacate, ethyl 5-hydroxyhexanoate, ethyl 5-hydroxydecanoate, ethyl 5-hydroxyundecanoate, propyl 5-hydroxydecanoate, isopropyl 5-hydroxydecanoate, 2-methylpropyl 5-hydroxyoctanoate, ethyl 5-hydroxy-9-methyldecanoate, methyl 5-acetoxydecanoate, ethyl 5-acetoxydecanoate, benzyl acetate and benzyl propionate; lactones such as γ-caprolactone, γ-heptalactone, γ-octalactone, γ-nonalactone, γ-decalactone, 7-decen-4-olide, 3-methyl-4-decen-4-olide, 3-methyl-5-decen-4-olide, γ-undecalactone, γ-dodecalactone, γ-tridecalactone, γ-tetradecalactone, δ-caprolactone, 2-hexen-5-olide, 2-hepten-5-olide, 3-octalactone, 2-octen-5-olide, 4-methyl-5-octanolide, δ-nonalactone, 2-nonen-5-olide, 4-methyl-5-nonanolide, δ-decalactone, 2-decen-5-olide, 4-methyl-5-decanolide, δ-undecalactone, 2-undecen-5-olide, 4-methyl-5-undecanolide, δ-dodecalactone, 2-dodecen-5-olide, 4-methyl-5-dodecanolide, δ-tridecalactone, 2-tridecen-5-olide, 4-methyl-5-tridecanolide, δ-tetradecalactone, 2-tetradecen-5-olide, 2-pentadecen-5-olide, 2-hexadecen-5-olide, 2-heptadecen-5-olide, 2-octadecen-5-olide, 2-nonadecen-5-olide, 2-eicosen-5-olide, ε-decalactone and macrocyclic lactones represented by cyclopentadecanolide; ethers such as rose oxide, cedryl methyl ether, linalool oxide, menthofuran and theaspirane; fatty acids such propionic acid, butyric acid, 2-methylbutyric acid, valeric acid, isovaleric acid, caproic acid, trans-2-hexenoic acid, heptanoic acid, caprylic acid, nonanoic acid, 5-hydroxynonanoic acid, capric acid, 2-decenoic acid, 4-decenoic acid, 5-decenoic acid, 6-decenoic acid, 9-decenoic acid, 5-hydroxydecanoic acid, 5-hydroxyundecanoic acid, lauric acid, 5-hydroxydodecanoic acid, myristic acid, pentadecanoic acid, isopentadecanoic acid, palmitic acid, heptadecanoic acid, stearic acid, oleic acid, linoleic acid and linolenic acid; phenols such as eugenol, isoeugenol and 4-ethylguaiacol; nitrogen-containing compounds such as methyl anthranilate, trimethylamine, indole, skatole, pyridine, isoquinoline, pyrazine, methylpyrazine and geranyl nitrile; sulfur-containing compounds such as methanethiol, isobutyl mercaptan, 2,4-dithiapentane, dimethyl sulfide, dimethyl disulfide, dimethyl trisulfide, dimethyl sulfoxide, dimethyl sulfone, methylsulfonylmethane, methyl isothiocyanate, ethyl isothiocyanate, allyl isothiocyanate, 2-methyl-3-butanethiol, methional, ethyl thioacetate, methyl thiobutyrate, 3-butenyl isothiocyanate, 2-methylthiophene, benzothiazole, sulfurol, thiomethyl acetyllactate, thiomethyl propionyllactate, thiomethyl butyryllactate, thiomethyl valeryllactate, thiomethyl 2-methylbutyryllactate, thiomethyl desilyllactate, thioethyl acetyllactate, thoethyl propionyllactate, thoethyl butyryllactate, thoethyl valeryllactate and thiopropyl isocaproyllactate; natural extracts and natural essential oils such as oranges, lemons, bergamots, mandarins, peppermint, spearmint, lavenders, hyacinths, chamomiles, rosemary, eucalypti, sage, basil, roses, galbanum, geraniums, jasmines, ylang-ylangs, anises, cloves, ginger, nutmegs, cardamoms, cedars, cypresses, vetiver, patchouli and labdanum.

The perfume composition comprising the S-alkyl 5-[(1-alkoxy)ethoxy] alkanethioate may, if necessary, be used as the diluent or perfume-retaining agent solvent described above, which includes water, ethanol, ethylene glycol, propylene glycol, dipropylene glycol, 1,3-butylene glycol, glycerin, hexylene glycol, benzyl benzoate, triethyl citrate, diethyl phthalate, hercholine, fatty acid triglycerides, fatty acid diglycerides and the like.

The S-alkyl 5-[(1-alkoxy)ethoxy] alkanethioate has a characteristic aroma by itself, but with the passage of time, since it produces alkyl mercaptans (especially methyl mercaptan and ethyl mercaptan) reminiscent of a strong fatty feeling, cabbage-like, onion-like, garlic-like odor and the like, it also has use as a precursor for alkyl mercaptans.

As described above, the S-alkyl 5-[(1-alkoxy)ethoxy] alkanethioate may be used alone or as a perfume composition comprising an S-alkyl 5-[(1-alkoxy) ethoxy] alkanethioate to impart the above-mentioned aroma characteristics to fragrances and cosmetics or foods and bevarages, and to improve and enhance, an oily feeling, a fat feeling, a fermentation feeling, a rich feeling, a fresh feeling, an onion-like flavor, and a meat-like flavor.

Specific examples of foods and beverages that can improve or enhance aroma and flavor with the perfume composition comprising an S-alkyl 5-[(1-alkoxy)ethoxy] alkanethioate include, for example, cola beverages, carbonated beverages such as carbonated beverages containing fruit juices and carbonated beverages containing milks; soft drinks such as such as fruit juice beverages, vegetable beverages, sports drinks, honey beverages, soy milk, vitamin supplement beverages, mineral supplement beverages, nutritional drinks, nutritious drinks, lactic acid bacteria beverages and milk beverages; taste beverages such as green tea, black tea, oolong tea, herbal tea, milk tea, milk coffee, coffee drinks; alcoholic beverages such as chuhai, cocktail drinks, low-malt beer, fruit wine, condiment wine; dairy products such as butter, cheese, milk and yogurt; desserts such as ice cream, low-fat ice cream, ice, yogurt, custard pudding, jelly, dairy desserts, and mixes for the production thereof, confectionery such as caramels, candies, candy tablets, crackers, biscuits, cookies, pies, chocolate, snack foods, and mixes such as a cake mix for the production thereof, and general foods such as bread, soup and various instant foods, but are not limited thereto.

Specific examples of fragrances and cosmetics that can improve or enhance aromas with the perfume composition comprising an S-alkyl 5-[(1-alkoxy)ethoxy] alkanethioate include, for example, fragrance products, foundations, make up cosmetics, hair cosmetics, suntan cosmetics, medicated cosmetics, hair care products, soaps, body shampoo, detergents for kitchens, bath agents, detergents, fabric softener, bleaches, aerosol agents, deodorants and aromatics, repellents, compositions for the oral cavity, skin external preparations, pharmaceuticals, and the like, but are not limited thereto.

The amount of the S-alkyl 5-[(1-alkoxy)ethoxy]alkanethioate blended in the range of, for example, 0.01% ($1.0 \times 10^2$ ppm) to 10% ($1.0 \times 10^5$ ppm), preferably 0.05% ($5.0 \times 10^2$ ppm) to 5.0% ($5.0 \times 10^4$ ppm), more preferably 0.1% ($1.0 \times 10^3$ ppm) to 1.0% ($1.0 \times 10^4$ ppm) in the perfume composition can be illustrated.

The amount of the perfume composition in the product to be used varies depending on the purpose or the type of the target, but the amount of the S-alkyl 5-[(1-alkoxy)ethoxy] alkanethioate is 1 ppb to 100 ppm relative to the total amount. Preferably, a range of 2 ppb to 50 ppm, more preferably, a range of 10 ppb to 10 ppm can be exemplified. Within these ranges, the fragrances and cosmetics or foods and beverages have an excellent effect of imparting or enhancing an aroma and flavor having an oily feeling, a fatty feeling, a fermenting feeling, a rich feeling, a fresh feeling.

Hereinafter, the disclosures or the subject matters of the specification will be described more specifically with reference to examples. Note that these examples are not intended to limit the technical scope of the present subject matters to these.

EXAMPLES

In the Examples, the measurement of reaction crude products and purified products was performed using the following analytical instruments.

GC measurement: GC-2014 (manufactured by Shimadzu Corporation) and Chromatopack C-R8A (manufactured by Shimadzu Corporation) GC column: TC-1 manufactured by GL Sciences Inc. (length 30 m, inner diameter 0.53 mm, liquid layer thickness 1.50 micrometers) GC/MS measurement: 5973N (manufactured by Agilent) GC column: TC-1701 manufactured by GL Sciences Inc. (length 30 m, inner diameter 0.25 mm, liquid layer thickness 0.25 micrometer) NMR measurement: ECX-400A (manufactured by JEOL RESONANCE).

Example 1

Synthesis of ethyl 5-hydroxydecanoate

In a 10 L four-necked flask, δ-decalactone (manufactured by Tokyo Chemical Industry Co., Ltd., 1500.0 g, 0.10 mol), 99% ethanol (3000.0 g), and a strongly acidic cation exchange resin (SK1B-H+, 45.0 g) were added. The mixture was stirred at 80±5° C. for 3 hours, and then stirred at room temperature overnight. The resin was separated by filtration through filter paper, and then concentrated under vacuum. The obtained concentrate was dried under reduced pressure to obtain crude ethyl 5-hydroxydecanoate (1826.5 g, purity 89.1%).

Example 2

Synthesis of ethyl 5-[(1-ethoxy) ethoxy] decanoate

The crude product of Example 1 and toluene (3650.0 g) were charged into a 10 L four-necked flask, and the mixture was stirred under ice-water cooling. Pyridinium para-toluenesulfonate (44.3 g, 0.2 mol) was added thereto, and ethyl vinyl ether (1270.1 g, 17.6 mol) was added dropwise at 5° to 10° C./1 hour. The mixture was stirred at the same temperature for 1 hour and at room temperature overnight. This was poured into a saturated aqueous solution of sodium carbonate (4.4 kg), separated, and the obtained organic layer was washed with 5% saline, dried over anhydrous magnesium sulfate powder, and concentrated under vacuum. The obtained concentrate (2738.0 g) was subjected to precision distillation to obtain ethyl 5-[(1-ethoxy)ethoxy]decanoate (1385.1 g) (yield 2 steps 54.5%).

Example 3

Synthesis of S-methyl 5-[(1-ethoxy)ethoxy]decanethioate

Potassium hydroxide (70.1 g, 1.3 mol) and 95% ethanol (1380.0 g) were charged into a 3 L four-necked flask and stirred at room temperature. Ethyl 5-[(1-ethoxy)ethoxy] decanoate (300.0 g, 1.1 mol) was added thereto, and the mixture was stirred overnight at the same temperature. The reaction solution was concentrated under vacuum to obtain a crudely purified yellow solid (345.9 g).

The crude product (345.9 g) obtained in the previous steps, ether (3000 mL) and triethylamine (105.2 g, 1.1 mol) were charged into a 5 L four-necked flask, and the mixture was stirred under ice-water cooling. Pivaloyl chloride (150.7 g, 1.3 mol) was added dropwise thereto at 5° C. to 10° C./30 minutes. The mixture was stirred for 30 minutes under ice-water cooling and for 7 hours at room temperature. The obtained reaction solution was directly used for the next step.

A 10 L four-necked flask was charged with a 15% aqueous solution of methyl mercaptan sodium salt (878.5 g, 1.9 mol) and stirred under ice-water cooling. The reaction solution obtained in the previous steps was added dropwise thereto at a temperature of 10° C. to 20° C. /30 minutes. After the completion of the addition, the mixture was stirred at room temperature overnight. The reaction solution was separated, and the aqueous layer was extracted with ether (500 mL). The organic layers were combined, washed sequentially with a saturated aqueous solution of sodium hydrogencarbonate (1500 mL) and a saturated aqueous solution of sodium chloride (1500 mL), and dried over anhydrous sodium sulfate. The mixture was concentrated under vacuum, and the obtained crude product (275.6 g) was distilled to obtain S-methyl 5-[(1-ethoxy)ethoxy]decanethioate (the present product 1: 190.5 g) (yield 3 steps 63.1%).

Physical property data of S-methyl 5-[(1-ethoxy)ethoxy] decanethioate $^1$H-NMR (400 MHz, $C_6D_6$): δ ppm
4.64-4.59 (m, 1H), 3.48-3.35 (m, 3H), 2.41 (t, 1H, J=7.4 Hz), 2.33 (t, 1H, J=7.4 Hz), 1.99 (s, 3H), 1.86-1.62 (m, 2H), 1.55-1.34 (m, 5H), 1.32-1.20 (m, 8H), 1.13 (q, 3H, J=6.5 Hz), 0.91-0.87 (m, 3H)

$^{13}$C-NMR (100 MHz, $C_6D_6$): δ ppm 198.36, 198.27, 98.87, 98.73, 75.69, 75.51, 59.83, 59.67, 44.09, 44.07, 35.03, 34.38, 34.17, 33.48, 32.44, 32.42, 25.44, 25.07, 23.05, 23.01, 21.99, 21.53, 20.75, 15.68, 15.64, 14.29, 14.26, 11.18

Example 4

Synthesis of ethyl 5-hydroxytetradecanoate

In a 200 mL four-necked flask, δ-tetradecalactone (manufactured by Tokyo Chemical Industry Co., Ltd., 45.3 g, 0.20 mol), 99% ethanol (90.6 g), and a strongly acidic cation exchange resin (SK1B-H+, 1 g) were added. The mixture was stirred at 80±5° C. for 5 hours, and then stirred at room temperature overnight. After stirring at room temperature overnight, the resin was separated by filtration through a filter paper and concentrated under vacuum to obtain crude ethyl 5-hydroxytetradecanoate (60.7 g).

Example 5

Synthesis of ethyl 5-[(1-ethoxy)ethoxy]tetradecanoate

The crude (60.7 g) of Example 4 and toluene (30.0 g) were charged into a 200 mL four-necked flask, and the mixture was stirred under ice-water cooling. Pyridinium para-toluenesulfonate (1.0 g, 4.0 mmol) was added thereto, and ethyl vinyl ether (22.8 g, 0.40 mol) was added dropwise at 3° C./10 minutes. After stirring under ice-water cooling for 2.5 hours, the mixture was stirred at room temperature for 1 hour. After the reaction mixture has been poured into a saturated aqueous solution of sodium carbonate (100 mL), the layers were separated, and the organic layer was washed with 5% saline and dried over anhydrous magnesium sulfate. The residue was concentrated under vacuum, and the obtained concentrated residue (68.1 g) was purified by silica gel column chromatography (850 g of silica gel, n-hexane/ethyl acetate=1/0→20/1→10/1) to obtain the desired product. Ethyl 5-[(1-ethoxy)ethoxy]tetradecanoate (50.6 g) was obtained as a colorless oil. 73% yield from δ-tetradecalactone.

Example 6

Synthesis of S-methyl 5-[(1-ethoxy)ethoxy]tetradecanethioate

Under a nitrogen atmosphere, a 100 mL flask was charged with ethyl 5-[(1-ethoxy)ethoxy]tetradecanoate (10.3 g, 30.0 mmol) obtained in the previous steps and 95% ethanol (38.0 g), and stirred at room temperature. Potassium hydroxide (2.0 g, 36.0 mmol) was added thereto, and the mixture was stirred at room temperature for 8 hours. To this was added sodium hydrogen carbonate (1.0 g, 12.0 mmol), and the mixture was stirred overnight. The reaction solution was concentrated under reduced pressure to obtain a crude yellow solid (10.7 g), which was directly used in the next step.

The crude product (10.7 g) obtained in the previous steps, ether (107 mL) and triethylamine (0.30 g, 3.0 mmol) were charged into a 200 mL flask, and the mixture was stirred under ice-water cooling. Pivaloyl chloride (3.7 mL, 30.0 mmol) was added dropwise thereto over 15 minutes. The solution stirred for 1 hour under ice-water cooling was subjected to the next step.

A 200 mL four-necked flask was charged with a 15% aqueous solution of methyl mercaptan sodium salt (21.0 g, 45.0 mmol) and stirred under ice-water cooling. The whole amount of the above reaction solution was added dropwise thereto over 15 minutes, and the mixture was stirred under ice-water cooling for 30 minutes and at room temperature for 2 hours. After standing overnight, the layers were separated and the resulting aqueous layer was extracted with ether. The organic layers were combined, washed sequentially with an aqueous sodium hydrogen carbonate solution and saturated saline, and dried over anhydrous sodium sulfate. It was concentrated under vacuum, and the obtained crude product (8.6 g) was purified by silica gel column chromatography (silica gel 150 g, n-hexane/ethyl acetate=1/0→50/1→30/1) to obtain the desired product. S-methyl 5-[(1-ethoxy)ethoxy]tetradecanethioate (the present product 2: 5.9 g) was obtained as a colorless oil. 57% yield from ethyl 5-[(1-ethoxy)ethoxy]tetradecanoate.

Physical property data of S-methyl 5-[(1-ethoxy)ethoxy]tetradecanethioate
$^1$H-NMR (400 MHz, CDCl$_3$): δ ppm
4.67-4.62 (m, 1H), 3.52-3.38 (m, 3H), 2.43 (t, 1H, J=7.4 Hz), 2.34 (t, 1H, J=7.4 Hz), 2.00 (s, 3H), 1.89-1.65 (m, 2H), 1.60-1.37 (m, 5H), 1.29-1.27 (m, 16H), 1.16 (dt, 3H, J=7.0 Hz, 2.1 Hz), 0.93-0.90 (m, 3H)
$^{13}$C-NMR (100 MHz, CDCl$_3$): δ ppm 198.35, 198.26, 98.87, 98.72, 75.71, 75.51, 59.83, 59.69, 44.09, 35.12, 34.47, 34.19, 33.48, 32.29, 30.33, 30.30, 30.11, 30.07, 30.03, 29.76, 25.82, 25.45, 23.08, 22.01, 21.53, 20.75, 15.68, 14.33, 11.18

Example 7

Aroma Evaluation 0.1% of each of S-methyl 5-[(1-ethoxy)ethoxy]decanothioate (Product 1 of the present invention) and S-methyl 5-[(1-ethoxy)ethoxy] tetradecanethioate (Product 2 of the present invention) The ethanol solution was evaluated for aroma by five well-trained panelists. The aroma evaluation was performed by preparing the 0.1% ethanol solution in a 30 mL sample bottle and using an odor paper impregnated with the aroma at the mouth of the bottle and the solution. Table 1 shows the average odor evaluation of the five persons.

TABLE 1

| Aroma evaluation | |
|---|---|
| Compound | Aroma evaluation |
| S-Methyl 5-[(1-ethoxy)ethoxy]decanethioate (Inventive article 1) | Fermented milk-like feeling, heated milk-like feeling, oil and fat feeling, fat feeling and fresh feeling |
| S-Methyl 5-[(1-ethoxy)ethoxy]tetradecanethioate (Inventive article 2) | Fermented milk-like feeling, heated milk-like feeling, oil and fat feeling, fat feeling and fresh feeling |

Example 8

Effect of Addition to Milk-Like Preparation Flavor Composition

Each component (% by mass) in Table 2 was prepared as a milk-like prepared flavor composition. 2.0 g of the product 1 of the present invention or the product 2 of the present invention was mixed with the milk-like mixed flavor composition (comparative product 1) to prepare a new milk-like mixed flavor composition. Sensory evaluation was performed on these inventive product 3 and inventive product 4 (wherein inventive product 1 and inventive product 2 were mixed, respectively) and comparative product 1 by 10 well-trained panelists.

TABLE 2

| Milk-like prepared flavor formulation | | | |
|---|---|---|---|
| | Comparative product 1 | Inventive product 3 | Inventive product 4 |
| Vanillin | 25.0 | 25.0 | 25.0 |
| Ethyl vanillin | 35.0 | 35.0 | 35.0 |
| Cyclotene | 2.5 | 2.5 | 2.5 |
| Ethyl maltol | 3.5 | 3.5 | 3.5 |
| γ-Nonalactone | 10.0 | 10.0 | 10.0 |
| γ-Decalactone | 2.5 | 2.5 | 2.5 |
| δ-Decalactone | 2.5 | 2.5 | 2.5 |
| γ-Undecalactone | 2.0 | 2.0 | 2.0 |
| Acetylmethylcarbinol | 3.0 | 3.0 | 3.0 |
| Diacetyl | 7.0 | 7.0 | 7.0 |
| Butyric acid | 5.0 | 5.0 | 5.0 |
| Propylene glycol | 902.0 | 900.0 | 900.0 |
| Inventive product 1 | — | 2.0 | — |
| Inventive product 2 | — | — | 2.0 |
| Total | 1000.0 | 1000.0 | 1000.0 |

As a result, all 10 panelists evaluated that the product 3 of the present invention and the product 4 of the present invention emphasized a good feeling of fermented milk and heated milk compared to the comparative product 1.

Example 9

Effect of Addition to Butter-Like Compounded Flavor Composition

Each component (% by mass) in Table 3 was prepared as a butter-like prepared flavor composition. Then, 5.0 g of the present invention product 1 or the present invention product 2 was mixed with the butter-like compounded flavor composition of Table 3 (comparative product 2) to prepare a novel butter-like compounded flavor composition. Sensory evaluation was performed on 1 the invention products 5 and 6 (obtained by mixing the invention product 1 and the invention product 2, respectively) and the comparison product 2 with 10 well-trained panelists.

TABLE 3

Butter-like prepared perfume formulation

| | Comparative product 2 | Inventive product 5 | Inventive product 6 |
|---|---|---|---|
| Methyl undecyl ketone | 2.0 | 2.0 | 2.0 |
| δ-Decalactone | 27.0 | 27.0 | 27.0 |
| δ-Dodecalactone | 58.0 | 58.0 | 58.0 |
| Butyric acid | 4.0 | 4.0 | 4.0 |
| Methyl heptyl ketone | 0.4 | 0.4 | 0.4 |
| γ-Decalactone | 0.6 | 0.6 | 0.6 |
| Acetylmethylcarbinol | 8.0 | 8.0 | 8.0 |
| Vegetable oil | 900.0 | 895.0 | 895.0 |
| Inventive product 1 | — | 5.0 | — |
| Inventive product 2 | — | — | 5.0 |
| Total | 1000.0 | 1000.0 | 1000.0 |

As a result, all 10 panelists evaluated that the inventive product 5 and the inventive product 6 emphasized a good feeling of fermented milk and heated milk compared to the comparative product 2.

Example 10

Effect of Addition to Hyacinth-Like Blended Fragrance Composition

Each component (% by mass) shown in Table 4 below was prepared as a hyacinth-like prepared fragrance composition. A novel hyacinth-like compounded fragrance composition was prepared by mixing 5.0 g of the product 1 of the present invention or the product 2 of the present invention with the hyacinth-like compounded fragrance composition of Table 4 (comparative product 3). Sensory evaluation was performed on these inventive product 7 and inventive product 8, wherein inventive product 1 and inventive product 2 were mixed, respectively, and comparative product 3 by 10 well-trained panelists.

TABLE 4

Hyacinth-like basic prepared fragrance composition

| Blended component | Comparative product 3 | Inventive product 7 | Inventive product 8 |
|---|---|---|---|
| Phenylacetaldehyde | 100.0 | 100.0 | 100.0 |
| Cinnamic alcohol | 150.0 | 150.0 | 150.0 |
| Hyacinth absolute | 10.0 | 10.0 | 10.0 |

TABLE 4-continued

Hyacinth-like basic prepared fragrance composition

| Blended component | Comparative product 3 | Inventive product 7 | Inventive product 8 |
|---|---|---|---|
| Phenyl ethyl alcohol | 100.0 | 100.0 | 100.0 |
| α-Ionone | 30.0 | 30.0 | 30.0 |
| Benzyl propionate | 70.0 | 70.0 | 70.0 |
| Ylang-ylang oil | 10.0 | 10.0 | 10.0 |
| Amylcinnamic aldehyde | 50.0 | 50.0 | 50.0 |
| Isoeugenol | 40.0 | 40.0 | 40.0 |
| Benzyl alcohol | 100.0 | 100.0 | 100.0 |
| Dimethyl benzyl carbinol | 30.0 | 30.0 | 30.0 |
| Galbanum resinoid | 30.0 | 30.0 | 30.0 |
| Phenylacetaldehyde dimethyl acetal | 80.0 | 80.0 | 80.0 |
| Lauryl alcohol | 20.0 | 20.0 | 20.0 |
| Nerol | 80.0 | 80.0 | 80.0 |
| Heliotropin | 60.0 | 60.0 | 60.0 |
| Dipropylene glycol | 40.0 | 35.0 | 35.0 |
| Inventive product 1 | — | 5.0 | — |
| Inventive product 2 | — | — | 5.0 |
| Total | 1000.0 | 1000.0 | 1000.0 |

As a result, all 10 panelists evaluated that the present invention product 7 and the present invention product 8 emphasized the rich aroma of hyacinth as compared with the comparative product 3.

Example 11

Effect by Addition of the Inventive Product 1 to Coffee

A coffee (control product 1) was prepared according to the coffee preparation formulation of Table 5 (% by mass).

TABLE 5

Coffee formulation

| | (g) |
|---|---|
| Coffee extract Bx. 2.7 | 500.0 |
| Sucrose | 60.0 |
| pH regulator (sodium hydrogencarbonate) | 1.0 |
| Water | 439.0 |
| Total | 1000.0 |

To 1000 g of coffee (control product 1), a 1% solution of the inventive product 1 obtained by diluting the product 1 with ethanol and then further diluting with water was added, respectively, in the amount of 10 μg (additional concentration of 0.1 ppb of the inventive product 1: comparative product 4), 100 μg (additional concentration of 1 ppb of the inventive product 1: inventive product 9), 1 mg (additional concentration of 10 ppb of the inventive product 1: inventive product 10), 10 mg (additional concentration of 100 ppb of the inventive product 1: inventive product 11), 100 mg (additional concentration of 1 ppm of the inventive product 1: inventive product 12), 1 g (additional concentration of 10 ppm of the inventive product 1: inventive product 13), 10 g (additional concentration of 100 ppm of the inventive product 1: inventive product 14) and 100 g (additional concentration of 1000 ppm of the inventive product 1: comparative product 5) to prepare coffee of the comparative products 4 and 5, and the inventive products 9 to 14. The flavor of each coffee was evaluated by 10 well-trained panelists. Table 6 shows the comparative evaluation with the control product 1 to which the product 1 of the present invention was not added.

TABLE 6

Flavor evaluation of Coffee

| | Concentration of Inventive product 1 added | Flavor evaluation |
|---|---|---|
| Comparative product 4 | 0.1 ppb | Almost the same as Control product |
| Inventive product 9 | 1 ppb | The flavor of coffee having a fresh feeling is increased slightly as compared with Control product. |
| Inventive product 10 | 10 ppb | A good flavor of coffee having a fresh feeling is increased as compared with Control product. |
| Inventive product 11 | 100 ppb | A good flavor of coffee having a fresh feeling is increased as compared with Control product. |
| Inventive product 12 | 1 ppm | A good flavor of coffee having a fresh feeling is increased as compared with Control product. |
| Inventive product 13 | 10 ppm | A good flavor of coffee having a fresh feeling and a slightly heavy oil and fat feeling are increased as compared with Control product. |
| Inventive product 14 | 100 ppm | A fresh feeling is increased remarkably, and a heavy oil and fat feeling is also increased as compared with Control product. |
| Comparative product 5 | 1000 ppm | A fresh feeling and an oil and fat feeling are extraneously strong, and a flavor the coffee has originally is lost. |

From the results shown in Table 6, it was found that the inventive products 9 to 14 had a fresh feeling and enhanced the aroma of coffee. In particular, the inventive products 11 and 12 are imparted with a good fresh flavor of coffee, and the good coffee-like flavor is remarkably emphasized. On the other hand, the comparative product 4 was not much different from control product 1, and the comparative product 5 was evaluated as losing the original aroma of coffee.

Example 12

Effect of Adding the Inventive Product 2 to Coffee

To 1000 g of coffee (control product 1), a 1% solution of the inventive product 2 diluted with ethanol and then further diluted with water was added, respectively, in the amount of 10 µg (additional concentration of 0.1 ppb of the inventive product 2: comparative product 6), 100 µg (additional concentration of 1 ppb of the inventive product 2: inventive product 15), 1 mg (additional concentration of 10 ppb of the inventive product 2: inventive product 16), 10 mg (additional concentration of 100 ppb of the inventive product 2: inventive product 17), 100 mg (additional concentration of 1 ppm of the inventive product 2: present product 18), 1 g (additional concentration of 10 ppm of the inventive product 2: present product 19), 10 g (additional concentration of 100 ppm of the inventive product 2: inventive product 20) and 100 g (additional concentration of 1000 ppm of the inventive product 2: comparative product 7) to prepare coffee of the comparative products 6 and 7, and the inventive products 15 to 20. The flavor of each coffee was evaluated by 10 well-trained panelists. Table 7 shows the comparative evaluation with the control product 1 to which the inventive product 2 was not added.

TABLE 7

Flavor evaluation of Coffee

| | Concentration of Inventive product 2 added | Flavor evaluation |
|---|---|---|
| Comparative product 6 | 0.1 ppb | Almost the same as Control product |
| Inventive product 15 | 1 ppb | The flavor of coffee having a fresh feeling is increased slightly as compared with Control product. |
| Inventive product 16 | 10 ppb | A good flavor of coffee having a fresh feeling is increased as compared with Control product. |
| Inventive product 17 | 100 ppb | A good flavor of coffee having a fresh feeling is increased as compared with Control product. |
| Inventive product 18 | 1 ppm | A good flavor of coffee having a fresh feeling is increased as compared with Control product. |
| Inventive product 19 | 10 ppm | A good flavor of coffee having a fresh feeling and a slightly heavy oil and fat feeling are increased as compared with Control product. |
| Inventive product 20 | 100 ppm | A fresh feeling is increased remarkably, and a heavy oil and fat feeling is also increased as compared with Control product. |
| Comparative product 7 | 1000 ppm | A fresh feeling and an oil and fat feeling are extraneously strong, and a flavor the coffee has originally is lost. |

From the results shown in Table 7, the inventive products 15 to 20 were given a fresh feeling and the aroma of coffee was enhanced. In particular, the inventive products 17 and 18 are imparted with a good coffee fresh aroma, and the good coffee-like aroma is remarkably emphasized. On the other hand, the comparative product 6 was not much different from the control product 1, and the comparative product 7 was evaluated as losing the original aroma of coffee.

Example 13

Effect by Addition of the Inventive Product 1 to Ice Cream

An ice cream (control product 2) was prepared according to the ice cream preparation formulation of Table 8 (% by mass).

TABLE 8

Ice cream formulation

| | (g) |
|---|---|
| Milk | 500 |
| 40% fresh cream | 160 |
| Skim milk powder | 40 |
| Sugar | 100 |
| 70% starch sirup | 80 |
| Emulsifying and stabilizing agent | 5 |
| Water | 115 |
| Total | 1000 |

To 1000 g of ice cream (control product 2), a 1% solution of the product 1 of the present invention diluted with ethanol and further diluted with water was added, respectively, in the amount of 10 µg (additional concentration of 0.1 ppb of the inventive product 1: comparative product 8), 100 µg (additional concentration of 1 ppb of the inventive product 1:

inventive product 21), 1 mg (additional concentration of 10 ppb of the inventive product 1: inventive product 22), 10 mg (additional concentration of 100 ppb of the inventive product 1: inventive product 23), 100 mg (additional concentration of 1 ppm of the inventive product 1: inventive product 24), 1 g (additional concentration of 10 ppm of the inventive product 1: inventive product 25), 10 g (additional concentration of 100 ppm of the inventive product 1: inventive product 26), 100 g (additional concentration of 1000 ppm of the inventive product 1: comparative product 9) to prepare ice creams of the comparative products 8 and 9 and the inventive products 21 to 26. The flavor of each ice cream was evaluated by 10 well-trained panelists. Table 9 shows the comparative evaluation with the control product 2 to which the inventive product 1 was not added.

TABLE 9

Flavor evaluation of ice cream

| | Concentration of Inventive product 1 added | Flavor evaluation |
|---|---|---|
| Comparative product 8 | 0.1 ppb | Almost the same as Control product |
| Inventive product 21 | 1 ppb | A slight fat feeling is imparted, and a milk-like flavor is increased as compared with Control product. |
| Inventive product 22 | 10 ppb | A fat feeling is imparted, and a good milk-like flavor is increased as compared with Control product. |
| Inventive product 23 | 100 ppb | A refreshing fat feeling is imparted, and a good milk-like flavor is increased remarkably as compared with Control product. |
| Inventive product 24 | 1 ppm | A refreshing fat feeling is imparted, and a good milk-like flavor is increased remarkably as compared with Control product. |
| Inventive product 25 | 10 ppm | A slightly heavy fat feeling is imparted, and a milk-like flavor is increased remarkably as compared with Control product. |
| Inventive product 26 | 100 ppm | A heavy fat feeling is imparted, and a milk-like flavor is increased remarkably as compared with Control product. |
| Comparative product 9 | 1000 ppm | A milk feeling is so strong that a foul smell which is different from a flavor the ice cream has originally is felt. |

From the results shown in Table 9, the inventive products 21 to 26 were imparted with a feeling of fat and had an enhanced milk flavor. In particular, the inventive products 23 and 24 have a clear fatty feeling, and a good milky aroma is remarkably emphasized. On the other hand, the comparative product 8 was not so different from control product 2, and the comparative product 9 was evaluated as having an off-flavor different from the original aroma of ice cream.

Example 14

Effect of Adding the Inventive Product 2 to Ice Cream

To 1000 g of ice cream (control product 2), a 1% solution of the inventive product 2 diluted with ethanol and further diluted with water was added, respectively, in the amount of 10 µg (additional concentration of 0.1 ppb of the inventive product 2: comparative product 10), 100 µg (additional concentration of 1 ppb of the inventive product 2: inventive product 27), 1 mg (additional concentration of 10 ppb of the inventive product 2: inventive product 28), 10 mg (additional concentration of 100 ppb of the product 2: invention product 29), 100 mg (additional concentration of 1 ppm of the inventive product 2: invention product 30), 1 g (additional concentration of 10 ppm of the inventive product 2: invention product 31), 10 g (additional concentration of 100 ppm of the inventive product 2: inventive product 32) and 100 g (additional concentration of 1000 ppm of the inventive product 2: comparative product 11) to prepare ice creams of the comparative products 10 and 11, and the inventive products 27 to 32. The flavor of each ice cream was evaluated by 10 well-trained panelists. Table 10 shows the comparative evaluation with the control product 2 to which the inventive product 2 was not added.

TABLE 10

Flavor evaluation of ice cream

| | Concentration of Inventive product 2 added | Flavor evaluation |
|---|---|---|
| Comparative product 10 | 0.1 ppb | Almost the same as Control product |
| Inventive product 27 | 1 ppb | A slight fat feeling is imparted, and a milk-like flavor is increased as compared with Control product. |
| Inventive product 28 | 10 ppb | A fat feeling is imparted, and a good milk-like flavor is increased as compared with Control product. |
| Inventive product 29 | 100 ppb | A refreshing fat feeling is imparted, and a good milk-like flavor is increased remarkably as compared with Control product. |
| Inventive product 30 | 1 ppm | A refreshing fat feeling is imparted, and a good milk-like flavor is increased remarkably as compared with Control product. |
| Inventive product 31 | 10 ppm | A slightly heavy fat feeling is imparted, and a milk-like flavor is increased remarkably as compared with Control product. |
| Inventive product 32 | 100 ppm | A heavy fat feeling is imparted, and a milk-like flavor is increased remarkably as compared with Control product. |
| Comparative product 11 | 1000 ppm | A milk feeling is so strong that a foul smell which is different from a flavor the ice cream has originally is felt. |

From the results shown in Table 10, the inventive products 27 to 32 were imparted with a feeling of fat and had an enhanced milk flavor. In particular, the inventive products 29 and 30 have a clear fatty feeling and a good milky aroma is remarkably emphasized. On the other hand, the comparative product 10 was evaluated to be not much different from the control product 2, and the comparative product 11 was evaluated as having an off-flavor different from the original aroma of ice cream.

Example 15

Effect of Adding Milk-Like Preparation Flavor Composition to Milk Tea

The milk-like mixed flavoring composition obtained in Example 8 (the comparative product 1, the inventive product 3 and inventive product 4) was added to milk tea prepared according to the formulation in Table 11, and a milk tea beverage was prepared in a conventional method. Milk teas to which the comparative product 1, the inventive product 3 and inventive product 4 were added were designated as the comparative product 12, the inventive product 33 and inventive product 34, respectively. These milk teas were subjected to sensory evaluation by 20 well-trained panelists.

TABLE 11

Milk tea beverage formulation

|  | Comparative product 12 | Inventive product 33 | Inventive product 34 |
|---|---|---|---|
| Black tea extract | 420 | 420 | 420 |
| Granulated sugar | 120 | 120 | 120 |
| Milk | 230 | 230 | 230 |
| Whole fat milk powder | 20 | 20 | 20 |
| Skim milk powder | 10 | 10 | 10 |
| Sugar ester HLB 15 | 1 | 1 | 1 |
| Water | 198 | 198 | 198 |
| Comparative product 1 | 1 | 0 | 0 |
| Inventive product 3 | 0 | 1 | 0 |
| Inventive product 4 | 0 | 0 | 1 |
| Total (g) | 1000 | 1000 | 1000 |

As a result, all of the 20 panelists evaluated that the inventive product 33 and the inventive product 34 had a good feeling of fat and richness and were good compared with the comparative product 12.

Example 16

Effect of Adding Butter-Like Compounded Flavor Composition to Cookies

The butter-like compounded flavor composition obtained in Example 9 (the comparative product 2, the inventive product 5 and inventive product 6) was added to the cookie dough prepared according to the formulation in Table 12, and baked at 220° C. for 7 minutes to prepare cookies. Cookies to which the comparative product 2, the inventive product 5 and inventive product 6 were added were designated as the comparative product 13, the inventive product 35 and invention product 36, respectively. Sensory evaluation of these cookies was performed by 20 well-trained panelists.

TABLE 12

Cookie formulation

|  | Comparative product 13 | Inventive product 35 | Inventive product 36 |
|---|---|---|---|
| Wheat flour (low-gluten flour) | 500 | 500 | 500 |
| Sugar | 200 | 200 | 200 |
| Shortening (MP 37° C.) | 150 | 150 | 150 |
| Whole sweetened condensed milk | 50 | 50 | 50 |
| Whole fat milk powder | 20 | 20 | 20 |
| Common salt | 5 | 5 | 5 |
| Sodium bicarbonate | 4 | 4 | 4 |
| Ammonium bicarbonate | 5 | 5 | 5 |
| Water | 65 | 65 | 65 |
| Comparative product 2 | 1 | 0 | 0 |
| Inventive product 5 | 0 | 1 | 0 |
| Inventive product 6 | 0 | 0 | 1 |
| Total (g) | 1000 | 1000 | 1000 |

As a result, all of the 20 panelists evaluated that the inventive product 35 and the inventive product 36 had a unique creamy fat feeling and richness of butter were good compared with the comparative product 13.

Example 17

Effect of Adding Hyacinth-Like Compounded Fragrance Composition to Liquid Kitchen Detergent The hyacinth-like compounded fragrance composition obtained in Example 10 (the comparative product 3, the inventive product 7 and inventive product 8) was added to a kitchen liquid detergent prepared according to the formulation shown in Table 13, and the kitchen detergent was prepared in a conventional manner. The liquid detergent for kitchen to which the comparative product 3, the inventive product 7 and the inventive product 8 were added was designated as the comparative product 14, the inventive product 37 and the inventive product 38, respectively. Sensory evaluation of these kitchen liquid detergents was conducted by 20 well-trained panelists.

TABLE 13

Liquid detergent for kitchens formulation

|  | Comparative product 14 | Inventive product 37 | Inventive product 38 |
|---|---|---|---|
| Benzalkonium chloride | 1.0 | 1.0 | 1.0 |
| Citric acid | 5.0 | 5.0 | 5.0 |
| Diethylene glycol monobutyl ether | 3.0 | 3.0 | 3.0 |
| Xanthan gum | 0.5 | 0.5 | 0.5 |
| Alkyl glycoside | 2.0 | 2.0 | 2.0 |
| Water | 88.4 | 88.4 | 88.4 |
| Comparative product 3 | 0.1 | — | — |
| Inventive product 7 | — | 0.1 | — |
| Inventive product 8 | — | — | 0.1 |
| Total (g) | 100.0 | 100.0 | 100.0 |

As a result, all of the 20 panelists evaluated that the inventive product 37 and the inventive product 38 had a hyacinth-like aroma as compared with the comparative product 14 and emphasized the richness of the hyacinth.

The invention claimed is:

1. An S-alkyl 5-[(1-alkoxy)ethoxy]alkanethioate represented by the following formula (1):

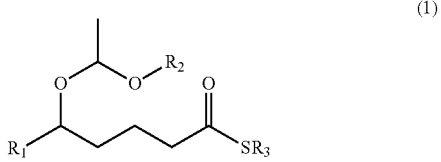

wherein $R_1$ represents an alkyl group having 1 to 9 carbon atoms, $R_2$ represents an alkyl group having 2 to 4 carbon atoms, and $R_3$ represents a methyl group or an ethyl group.

2. A composition comprising:

an S-alkyl 5-[(1-alkoxy)ethoxy]alkanethioate represented by the following formula (1):

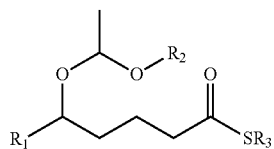

(1)

wherein $R_1$ represents an alkyl group having 1 to 9 carbon atoms, $R_2$ represents an alkyl group having 2 to 4 carbon atoms, and $R_3$ represents a methyl group or an ethyl group; and a diluent.

3. A fragrance and cosmetic or a food and beverage, comprising the compound of claim 1 and a diluent.

4. A method for imparting an aroma or a flavor to a fragrance and cosmetic or a food and beverage, or increasing an aroma or a flavor, comprising:

a step of adding, to a fragrance and cosmetic or a food and beverage in need of impartment or increasing of an aroma or a flavor, an effective amount of an S-alkyl 5-[(1-alkoxy)ethoxy]alkanethioate represented by the following formula (1):

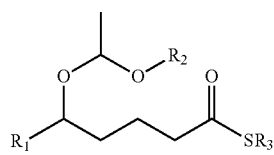

(1)

wherein $R_1$ represents an alkyl group having 1 to 9 carbon atoms, $R_2$ represents an alkyl group having 2 to 4 carbon atoms, and $R_3$ represents a methyl group or an ethyl group.

5. A fragrance and cosmetic or a food and beverage, comprising the composition of claim 2 and at least one other perfume component.

* * * * *